(12) United States Patent
Braithwaite

(10) Patent No.: US 7,571,723 B2
(45) Date of Patent: Aug. 11, 2009

(54) DELIVERY DEVICE

(75) Inventor: Philip Braithwaite, Tewkesbury (GB)

(73) Assignee: Innovata Biomed Limited, St. Albans (GB)

( * ) Notice: Subject to any disclaimer, the term of this patent is extended or adjusted under 35 U.S.C. 154(b) by 0 days.

(21) Appl. No.: 11/680,984

(22) Filed: Mar. 1, 2007

(65) Prior Publication Data

US 2007/0163580 A1 Jul. 19, 2007

Related U.S. Application Data

(62) Division of application No. 10/070,146, filed as application No. PCT/GB00/03377 on Sep. 4, 2000, now Pat. No. 7,219,665.

(30) Foreign Application Priority Data

Sep. 4, 1999 (GB) ................................. 9920839

(51) Int. Cl.
*A61M 15/00* (2006.01)
*A61M 16/00* (2006.01)

(52) U.S. Cl. .......................... 128/203.21; 128/203.15; 128/203.12; 128/203.19

(58) Field of Classification Search ............ 128/200.24, 128/203.12, 203.15, 203.19, 203.21; 221/92–133; 222/129–145.8, 153.02, 153.04
See application file for complete search history.

(56) References Cited

U.S. PATENT DOCUMENTS

| | | | |
|---|---|---|---|
| 1,858,735 A | 5/1932 | Goodsell | |
| 2,587,215 A | 2/1952 | Priestly | |
| 3,008,609 A | 11/1961 | Sessions | |
| 3,439,823 A | 4/1969 | Morane | |
| 3,603,058 A * | 9/1971 | Schubert | ...................... 53/525 |
| 3,798,054 A | 3/1974 | Kawata et al. | |
| 3,854,626 A | 12/1974 | Krechmar | |
| 3,874,381 A | 4/1975 | Baum | |
| 3,876,269 A | 4/1975 | Fisher et al. | |
| 4,047,635 A | 9/1977 | Bennett, Jr. | |
| 4,114,615 A | 9/1978 | Wetterlin | |
| 4,174,034 A | 11/1979 | Hoo | |

(Continued)

FOREIGN PATENT DOCUMENTS

DE 14 98 398 1/1969

(Continued)

OTHER PUBLICATIONS

Gerrity, T.R., "Pathophysiological and Disease Constraints on Aerosol Delivery," Chapter 1, *Respiratory Drug Delivery I*, ed. Byron, P.R., CRC Press, pp. 1-38 (1990).

*Primary Examiner*—Justine R Yu
*Assistant Examiner*—Annette F Dixon
(74) *Attorney, Agent, or Firm*—Nixon Peabody LLP

(57) ABSTRACT

A delivery device, e.g. an inhaler, comprises a rotatable metering member adapted to dispense a measured amount of material, a material delivery passage and a material delivery orifice and at least one actuator member adapted to move the metering member from a material retaining position to a material dispensing position. In a magazine comprising a plurality of metering members, the actuator and metering members may operate in a radial direction. A plurality of rotatable magazines may be utilized in the delivery device. The delivery device may be used to deliver a single or a combination therapy.

19 Claims, 10 Drawing Sheets

U.S. PATENT DOCUMENTS

| | | | |
|---|---|---|---|
| 4,200,099 A | 4/1980 | Guenzel et al. | |
| 4,274,403 A | 6/1981 | Struve | |
| 4,467,969 A * | 8/1984 | Godfrey et al. | 241/101.8 |
| 4,524,769 A | 6/1985 | Wetterlin | |
| 4,534,343 A | 8/1985 | Nowacki et al. | |
| 4,570,630 A | 2/1986 | Elliott et al. | |
| 4,604,847 A | 8/1986 | Moulding, Jr. et al. | |
| 4,624,442 A | 11/1986 | Duffy et al. | |
| 4,627,432 A | 12/1986 | Newell et al. | |
| 4,635,829 A | 1/1987 | Brittingham, Jr. | |
| 4,668,218 A | 5/1987 | Virtanen | |
| 4,811,731 A | 3/1989 | Newell et al. | |
| 4,860,740 A | 8/1989 | Kirk et al. | |
| 4,882,210 A | 11/1989 | Romberg et al. | |
| 4,895,719 A | 1/1990 | Radhakrishnan et al. | |
| 4,907,583 A | 3/1990 | Wetterlin et al. | |
| 4,934,358 A | 6/1990 | Nilsson et al. | |
| 4,950,365 A | 8/1990 | Evans | |
| 5,002,048 A | 3/1991 | Makiej, Jr. | |
| 5,007,419 A | 4/1991 | Weinstein et al. | |
| 5,042,472 A | 8/1991 | Bunin | |
| 5,053,237 A | 10/1991 | Hendricks et al. | |
| 5,064,083 A | 11/1991 | Alexander et al. | |
| 5,067,491 A | 11/1991 | Taylor, II et al. | |
| 5,113,855 A | 5/1992 | Newhouse | |
| 5,152,422 A | 10/1992 | Springer | |
| 5,154,326 A | 10/1992 | Chang et al. | |
| 5,161,524 A | 11/1992 | Evans | |
| 5,169,029 A | 12/1992 | Behar et al. | |
| 5,192,528 A | 3/1993 | Radhakrishnan et al. | |
| 5,207,217 A | 5/1993 | Cocozza et al. | |
| 5,208,226 A | 5/1993 | Palmer | |
| 5,239,992 A * | 8/1993 | Bougamont et al. | 128/203.15 |
| 5,253,782 A | 10/1993 | Gates et al. | |
| 5,263,475 A * | 11/1993 | Altermatt et al. | 128/203.15 |
| 5,295,479 A | 3/1994 | Lankinen | |
| 5,301,666 A * | 4/1994 | Lerk et al. | 128/203.15 |
| 5,320,714 A * | 6/1994 | Brendel | 128/203.15 |
| 5,347,999 A | 9/1994 | Poss et al. | |
| 5,351,683 A | 10/1994 | Chiesi et al. | |
| 5,394,868 A | 3/1995 | Ambrosio et al. | |
| 5,409,132 A | 4/1995 | Kooijmans et al. | |
| 5,411,175 A | 5/1995 | Armstrong et al. | |
| 5,415,162 A | 5/1995 | Casper et al. | |
| 5,435,301 A | 7/1995 | Herold et al. | |
| 5,437,267 A | 8/1995 | Weinstein et al. | |
| 5,437,270 A | 8/1995 | Braithwaite | |
| 5,447,151 A | 9/1995 | Bruna et al. | |
| 5,450,160 A | 9/1995 | Tianello et al. | |
| 5,458,135 A | 10/1995 | Patton et al. | |
| 5,485,939 A | 1/1996 | Tucker | |
| 5,503,144 A | 4/1996 | Bacon | |
| 5,520,166 A | 5/1996 | Ritson et al. | |
| 5,524,613 A | 6/1996 | Haber et al. | |
| 5,544,646 A * | 8/1996 | Lloyd et al. | 128/200.14 |
| 5,551,597 A | 9/1996 | Lambelet, Jr. et al. | |
| 5,562,231 A | 10/1996 | Lambelet, Jr. et al. | |
| 5,562,918 A | 10/1996 | Stimpson | |
| 5,575,280 A | 11/1996 | Gupte et al. | |
| 5,617,845 A * | 4/1997 | Poss et al. | 128/203.15 |
| 5,622,166 A | 4/1997 | Eisele et al. | |
| 5,653,227 A | 8/1997 | Barnes et al. | |
| 5,657,748 A | 8/1997 | Braithwaite | |
| 5,657,794 A | 8/1997 | Briner et al. | |
| 5,664,557 A | 9/1997 | Makiej, Jr. | |
| 5,664,697 A | 9/1997 | Lambelet, Jr. et al. | |
| 5,676,130 A | 10/1997 | Gupte et al. | |
| 5,678,538 A | 10/1997 | Drought | |
| D389,570 S | 1/1998 | Savolainen | |
| 5,740,792 A | 4/1998 | Ashley et al. | |
| 5,740,794 A | 4/1998 | Smith et al. | |
| 5,775,536 A | 7/1998 | Lambelet, Jr. et al. | |
| 5,778,873 A | 7/1998 | Braithwaite | |
| 5,785,049 A | 7/1998 | Smith et al. | |
| 5,799,821 A | 9/1998 | Lambelet, Jr. et al. | |
| 5,857,457 A | 1/1999 | Hyppölä | |
| 5,875,776 A | 3/1999 | Vaghefi | |
| 5,881,719 A | 3/1999 | Gottenauer et al. | |
| 5,896,855 A | 4/1999 | Hobbs et al. | |
| 5,904,139 A | 5/1999 | Hauser | |
| 5,921,237 A | 7/1999 | Eisele et al. | |
| 5,924,417 A | 7/1999 | Braithwaite | |
| 5,941,241 A | 8/1999 | Weinstein et al. | |
| 5,944,660 A | 8/1999 | Kimball et al. | |
| 5,955,439 A | 9/1999 | Green | |
| 5,981,549 A | 11/1999 | Viner | |
| 5,996,577 A * | 12/1999 | Ohki et al. | 128/203.15 |
| 6,006,747 A | 12/1999 | Eisele et al. | |
| 6,035,463 A | 3/2000 | Pawelzik et al. | |
| 6,065,471 A | 5/2000 | Schaeffer et al. | |
| 6,065,472 A | 5/2000 | Anderson et al. | |
| 6,076,521 A | 6/2000 | Lindahl et al. | |
| 6,089,227 A | 7/2000 | Nilsson | |
| 6,116,238 A | 9/2000 | Jackson et al. | |
| 6,116,239 A | 9/2000 | Volgyesi | |
| 6,119,688 A | 9/2000 | Whaley et al. | |
| 6,125,844 A | 10/2000 | Samiotes | |
| 6,138,668 A | 10/2000 | Patton et al. | |
| 6,158,675 A | 12/2000 | Ogi | |
| 6,196,218 B1 | 3/2001 | Voges | |
| 6,220,243 B1 | 4/2001 | Schaeffer et al. | |
| 6,234,167 B1 | 5/2001 | Cox et al. | |
| 6,240,918 B1 | 6/2001 | Ambrosio et al. | |
| 6,254,854 B1 | 7/2001 | Edwards et al. | |
| 6,273,085 B1 | 8/2001 | Eisele et al. | |
| 6,321,747 B1 | 11/2001 | Dmitrovic et al. | |
| 6,324,428 B1 | 11/2001 | Weinberg et al. | |
| 6,325,241 B1 | 12/2001 | Garde et al. | |
| 6,328,034 B1 | 12/2001 | Eisele et al. | |
| 6,347,629 B1 | 2/2002 | Braithwaite | |
| 6,418,926 B1 | 7/2002 | Chawla | |
| 6,443,146 B1 | 9/2002 | Voges | |
| 6,484,718 B1 | 11/2002 | Schaeffer et al. | |
| 6,523,536 B2 | 2/2003 | Fugelsang et al. | |
| 6,543,443 B1 | 4/2003 | Klimowicz et al. | |
| 6,553,987 B1 | 4/2003 | Davies | |
| 6,557,550 B1 | 5/2003 | Clarke | |
| 6,557,552 B1 | 5/2003 | Cox et al. | |
| 6,601,729 B1 | 8/2003 | Papp | |
| 6,616,914 B2 | 9/2003 | Ward et al. | |
| 6,675,839 B1 | 1/2004 | Braithwaite | |
| 6,698,425 B1 | 3/2004 | Widerström | |
| 6,810,873 B1 | 11/2004 | Haikarainen et al. | |
| 6,810,874 B1 | 11/2004 | Koskela et al. | |
| 6,845,772 B2 | 1/2005 | Braithwaite et al. | |
| 6,926,003 B2 | 8/2005 | Seppälä | |
| 2003/0075172 A1 | 4/2003 | Johnson et al. | |
| 2003/0116157 A1 | 6/2003 | Braithwaite et al. | |
| 2003/0136406 A1 | 7/2003 | Seppala | |
| 2004/0011357 A1 | 1/2004 | Braithwaite | |
| 2004/0101482 A1 | 5/2004 | Sanders | |
| 2004/0236282 A1 | 11/2004 | Braithwaite | |
| 2004/0251318 A1 | 12/2004 | Braithwaite | |
| 2005/0121023 A1 | 6/2005 | Braithwaite | |

FOREIGN PATENT DOCUMENTS

| | | |
|---|---|---|
| DE | 23 46 730 A | 4/1975 |
| DE | 32 43 731 A | 5/1984 |
| DE | 195 30 540 | 2/1997 |
| DE | 197 57 207 A1 | 6/1999 |
| EP | 0 045 522 A2 | 2/1982 |
| EP | 0 079 478 A1 | 5/1983 |
| EP | 0 166 294 B1 | 10/1989 |

| | | | | | | |
|---|---|---|---|---|---|---|
| EP | 0 372 777 B1 | 6/1990 | | WO | WO 91/11495 | 8/1991 |
| EP | 0 424 790 B1 | 5/1991 | | WO | WO 91/14422 | 10/1991 |
| EP | 0 448 204 B1 | 9/1991 | | WO | WO 92/00771 A | 1/1992 |
| EP | 0 469 814 A1 | 2/1992 | | WO | WO 92/03175 | 3/1992 |
| EP | 0 514 085 B1 | 11/1992 | | WO | WO 92/04928 | 4/1992 |
| EP | 0 520 440 A1 | 12/1992 | | WO | WO 92/09322 | 6/1992 |
| EP | 0 539 469 B1 | 5/1993 | | WO | WO 92/18188 | 10/1992 |
| EP | 0 548 605 B1 | 6/1993 | | WO | WO 93/00951 | 1/1993 |
| EP | 0 573 128 A2 | 12/1993 | | WO | WO 93/11746 | 6/1993 |
| EP | 0 626 689 B1 | 11/1994 | | WO | WO 93/16748 | 9/1993 |
| EP | 0 659 432 A1 | 6/1995 | | WO | WO 95/00128 | 1/1995 |
| EP | 0 663 815 B1 | 7/1995 | | WO | WO 95/15777 | 6/1995 |
| EP | 1 062 962 A | 12/2000 | | WO | WO 97/00399 | 1/1997 |
| EP | 1 106 196 A | 6/2001 | | WO | WO 98/26828 | 6/1998 |
| EP | 1 208 863 A | 5/2002 | | WO | WO 98/30262 | 7/1998 |
| FR | 2 516 387 A | 5/1983 | | WO | WO 98/31352 | 7/1998 |
| FR | 2 584 604 A | 1/1987 | | WO | WO 99/13930 | 3/1999 |
| FR | 2 662 936 A | 12/1991 | | WO | WO 99/26676 | 6/1999 |
| FR | 2 753 791 A1 | 3/1998 | | WO | WO 99/12597 | 9/1999 |
| GB | 3908 | 3/1911 | | WO | WO 00/12163 | 3/2000 |
| GB | 1 242 211 | 8/1971 | | WO | WO 00/45878 | 8/2000 |
| GB | 1 573 551 | 8/1980 | | WO | WO 00/64519 | 11/2000 |
| GB | 2 041 763 A | 9/1980 | | WO | WO 01/17595 A | 3/2001 |
| GB | 2 165 159 A | 4/1986 | | WO | WO 01/39823 A | 6/2001 |
| GB | 2 178 965 A | 2/1987 | | WO | WO 01/51030 A1 | 7/2001 |
| GB | 2 235 753 A | 3/1991 | | WO | WO 01/60341 A1 | 8/2001 |
| GB | 2 248 400 A | 4/1992 | | WO | WO 01/87378 A2 | 11/2001 |
| GB | 2 366 208 A | 3/2002 | | WO | WO 02/056948 A | 7/2002 |
| WO | WO 90/07351 | 7/1990 | | WO | WO 2004/091705 A | 10/2004 |
| WO | WO 91/04011 | 4/1991 | | | | |
| WO | WO 91/11173 | 8/1991 | | * cited by examiner | | |

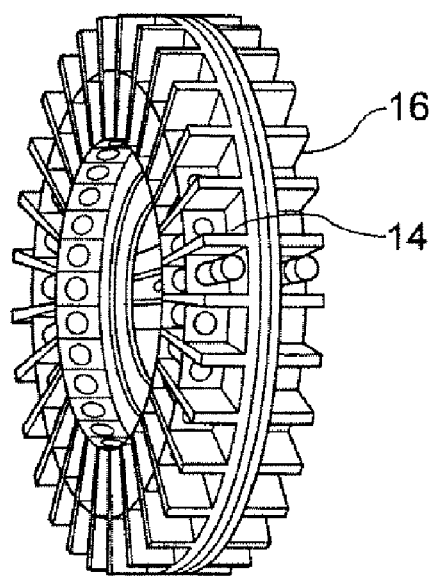
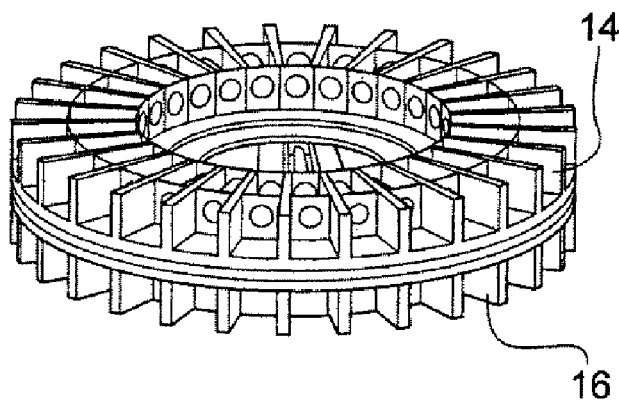
Fig. 4a    Fig. 4b
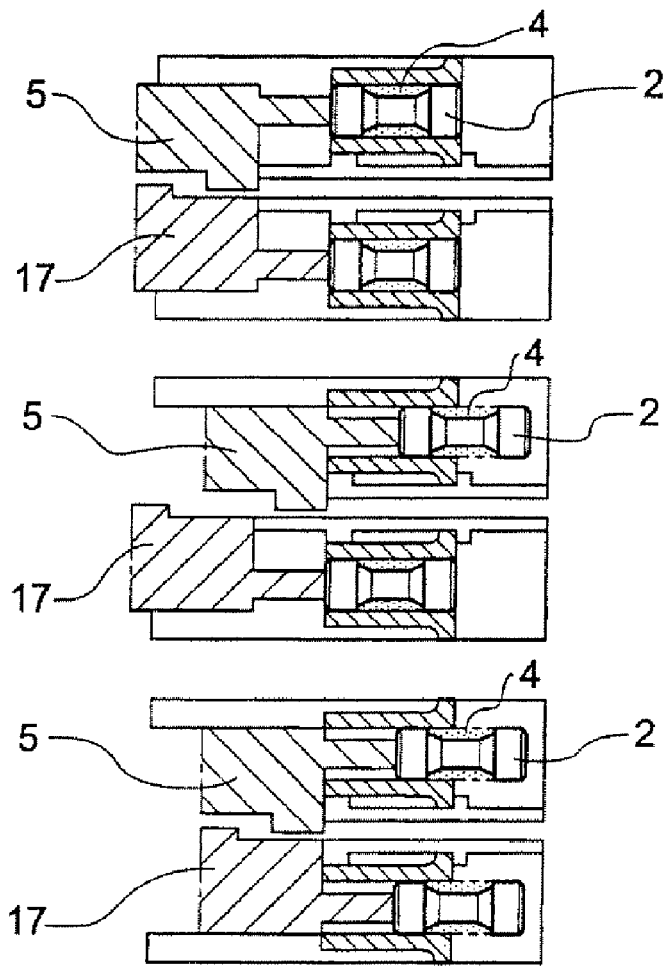
Fig. 5

DELIVERY DEVICE

The present application is a division of U.S. patent application Ser. No. 10/070,146 filed May 24, 2002, now U.S. Pat. No. 7,219,665, issued May 22, 2007, which is a U.S. national phase application based on PCT International Application No. PCT/GB00/03377, filed Sep. 4, 2000, which claims priority from British Patent Application No. GB 9920839.9, filed Sep. 4, 1999, all of which are hereby incorporated by reference in their entirety.

FIELD OF INVENTION

This invention relates to a novel form of material delivery device, for example, a medicament delivery device, such as an inhaler. In particular the invention provides a novel form of dry powder inhaler and a method of delivering a medicament.

BACKGROUND OF THE INVENTION

Dry powder inhalers are known, such as TECHNOHALER, being developed by Innovata Biomed in the UK. Such a device is described in International Patent Application No. WO 93/16748 (PCT/GB93/00335). WO '748 describes an inhaler which comprises a disc like magazine having a plurality of medicament carrying receptacles around its periphery. Each receptacle comprises a spool housed in a spool carrier. Each spool has a flange at each end which form a tight slidable fit within the body of the spool carrier. The space left between the body of the spool and the spool carrier is filled with an appropriate medicament.

The known TECHNOHALER is provided with suitable indexing means, including a push button and a ratchet mechanism which engages with the upper surface of the disc. Depression of the push button urges a push rod to push the spool, which is adjacent the inhalation passage of the inhaler, downwards and almost fully out of the spool carrier, and into the inhalation passage. As the spool is pushed into the inhalation passage, it carries with it the measured quantity of medicament which it has been used to contain inside the magazine. The user can then inhale through the mouthpiece so as to take up the drug now released into the inhalation passage. The upper flange of the spool remains, however, held by the lower part of the receptacle. When the user then releases push button, the ratchet mechanism causes the disc to rotate by one step so that the next receptacle is brought into register with the inhalation passage. The inhaler is thus reset and ready for delivery of another dose of drug. The "empty" spool not having been pushed fully out of the first receptacle, continues to move round with the first receptacle, supported by the lower guide.

In the inhaler of the prior art whilst the spool magazine lies essentially in the same plane as the as the mouthpiece of the inhaler, the push rod acts on a spool in a perpendicular plane.

BRIEF SUMMARY OF THE INVENTION

We have now found a novel form of medicament delivery device in which a push rod lies in essentially the same plane as the delivery orifice of the device and actuates the spool in a direction which is coaxial with the delivery orifice of the device. Thus when a plurality of spools are arranged radially in a magazine, such that the longitudinal axis of the spools lie in the same plane as the magazine and the spool may be expressed radially from the magazine. This has the advantage that, inter alia, a significantly slimmer device may be produced. Furthermore, the radial expression of the spools means that more than one magazine can be placed in the device and thus, inter alia, the device may deliver higher dosages, combination therapies and/or provide medication over a longer period of time.

Thus, according to the invention we provide a delivery device comprising a rotatable metering member adapted to dispense a measured amount of material, a material delivery passage and a material delivery orifice, and at least one actuator member adapted to move the metering member from a material retaining position to a material dispensing position characterised in that the actuator member moves in a substantially radial direction and actuates the metering member in a substantially radial direction.

The device of the invention has utility in a variety of areas, including, for example, medicament delivery. Thus, it is especially suited as an inhaler and especially a dry power inhaler (DPI).

According to a preferred feature of the invention the device is provided with a plurality of metering members housed in a magazine, preferably a substantially circular magazine. In an especially preferred embodiment a plurality of magazines may be loaded into the delivery device of the invention, e.g. a pair of magazines.

When the metering member is in the medicament retaining position it is preferably out of communication with the inhalation passage and whilst the metering member is in the medicament dispensing position it is preferably in communication with the inhalation passage.

The metering member is of such dimensions as to be able to pass into the inhalation passage. The metering member may comprise those described in WO 93/16748. Thus, in one embodiment the metering member may comprise a spool housed in a spool carrier. The spool carrier acts as a conduit for the spool to communicate with the inhalation passage. Thus the spool will be provided with a flange at each end such that the flanges are in sealing engagement with the inner walls of the conduit and a space exists between the inner walls of the conduit and the non-flanged portion of the spool. In the filled metering member, the space is taken up by a measured dosage of medicament. Indeed, the plug, flanges and conduit are so dimensioned so as to predetermine the amount of medicament available. In an alternative embodiment of the invention the metering member may comprise a medicament container with a closed end and an open end, a cap adapted to abut the open end of the container and a sleeve adapted to overlap the open end of the container and the cap. Reference hereinafter to a spool and spool carrier is intended to encompass a capped cartridge as hereinbefore described.

The spool and spool carrier is generally that described in the prior art patent application. However, instead of the spool being mounted in a vertical position each spool is essentially horizontally mounted. For the sake of clarity, the spools are positioned in the same plane as the plane of the disc magazine. The push rod used to eject the spool from the spool carrier therefore operates radially from the centre of the disc and does not push the spool out of the disc plane.

The actuator member may comprise a push rod mechanism which may be substantially similar to that known conventionally save that it acts radially.

Alternatively, when a plurality of magazines is used the actuator member may, for example, comprise a pair of push rods.

As hereinbefore described a significant advantage of the device of the invention is that it can be used to deliver combination therapies if desirable.

Increasingly, patients are required to take more than one medicine and this is no less the case in the treatment of bronchial disorders. Thus, for example, combination therapies such as a steroid with a $\beta_2$ agonist, e.g. fluticasone and salmeterol, have been commercially successful. To date, the administration of such combination therapies comprises the use of a predetermined formulation either as a dry powder, e.g. in a gelatin capsule or a foil blister; or alternatively as a metered dose aerosol. However, this approach suffers from the disadvantage, inter alia, that the medical practitioner is restricted in that it is not possible to vary the quantities of the two medicaments administered. Thus, there has therefore been a long felt need for a dry powder inhalation system which permits the administration of combination therapies.

It is within the scope of this invention for more than two medicaments to be administered, however, it is considered most likely that dual combination therapies would be preferred by the medical profession. Thus the description hereinafter will generally refer to an inhaler adapted to administer a dual combination medicament, but it would be well understood by one skilled in the art that these references could be construed to multiple combinations.

Thus according to a further feature of the invention we provide a dry powder inhaler as hereinbefore described characterised in that the inhaler is adapted to take a plurality of disc magazines. The medicament encapsulated in the spool carriers of the two disc magazines may be the same or different. In one embodiment the medicaments are different and thus the inhaler is used to deliver a combination therapy. Alternatively, the medicament encapsulated by the spool carrier may itself be a combination therapy.

In a further embodiment of the invention a medicament delivery device, e.g. an inhaler, comprises a pair of disc magazines. Such a device may preferentially be provided with means for engaging a first magazine whilst disengaging a second magazine and which is moveable from an engaging to a disengaging position and vice-versa.

Such means may comprise male and female interlocking members. Preferentially, the disc magazine is provided with a female member and a drive means is provided with a male member.

In an especially preferred embodiment a drive plate is provided with a male member and is adapted to engage with the drive means.

The male member may comprise a resilient protrusion which is resiliently biased towards a second disc magazine, but is constructed so as to be urged to engage with a female member of a first disc magazine, such that when the urging means is removed the male member is biased towards and engages with the second magazine.

A variety of medicaments may be administered by using the inhaler of the invention, such medicaments may have a systemic or non-systemic activity on the patient. Such medicaments are generally (but not limiting) antibiotics, bronchodilators or other anti-asthma drugs. Such medicaments include, but are not limited to $\beta_2$-agonists, e.g. fenoterol, formoterol, pirbuterol, reproterol, rimiterol, salbutamol, salmeterol and terbutaline; non-selective beta-stimulants such as isoprenaline; xanthine bronchodilators, e.g. theophylline, aminophylline and choline theophyllinate; anticholinergics, e.g. ipratropium bromide; mast cell stabilisers, e.g. sodium cromoglycate and ketotifen; bronchial anti-inflammatory agents, e.g. nedocromil sodium; and steroids, e.g. beclomethasone dipropionate, fluticasone, budesonide and flunisolide; and combinations thereof.

Specific combinations of medicaments which may be mentioned include combinations of steroids, such as, beclomethasone dipropionate, fluticasone, budesonide and flunisolide; and combinations of two $\beta_2$-agonists, such as, formoterol and salmeterol. It is also within the scope of this invention to include combinations of one or more of the aforementioned steroids with one or more of the aforementioned $\beta_2$-agonists.

Further medicaments which may be mentioned include systemically active materials, such as, proteinaceous compounds and/or macromolecules, for example, hormones and mediators, such as insulin, human growth hormone, leuprolide and alpha interferon; growth factors, anticoagulants, immunomodulators, cytokines and nucleic acids.

When dual disc magazines are used the inhaler will be provided with two radially acting push rod mechanisms. These mechanisms may be adapted to operate together, independently or sequentially.

BRIEF DESCRIPTION OF THE DRAWINGS

The invention will now be illustrated by way of example only and with reference to the accompanying drawings, in which:

FIG. 4 is a perspective view of a combination therapy disc magazine;

FIG. 5 is a cross-sectional view of the combination therapy mechanism;

DETAILED DESCRIPTION OF THE INVENTION

Figure 1:
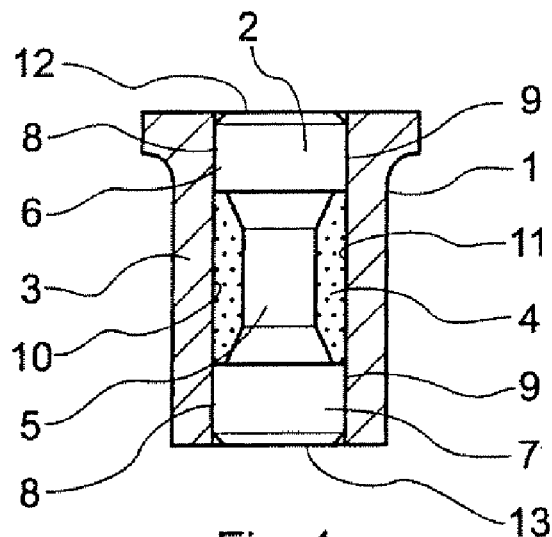
FIG. 1 is a cross-sectional view of a spool and spool carrier.

With reference to FIG. 1, a single medicament dose unit (1) is comprised of a spool (2), a spool carrier (3) and a single dose of medicament (4), for use in a dry powder inhaler. The spool (2) comprises a longitudinal body (5) and terminal flanges (6 and 7) at each end. The sides (8 and 9) of the flanges (6 and 7) form a seal and a tight slidable fit with the inner walls (10 and 11) of the spool carrier (3). The length of the spool (2) and the length of the spool carrier (3) are substantially the same. Each flange is provided with an external face (12 and 13).

Figure 2:
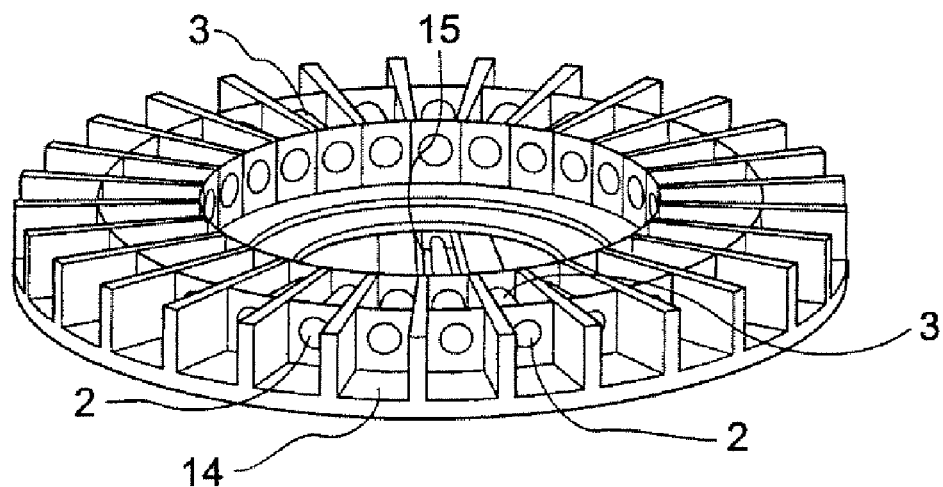
FIG. 2 is a perspective view of a single disc magazine comprising spools.
Figure 3:
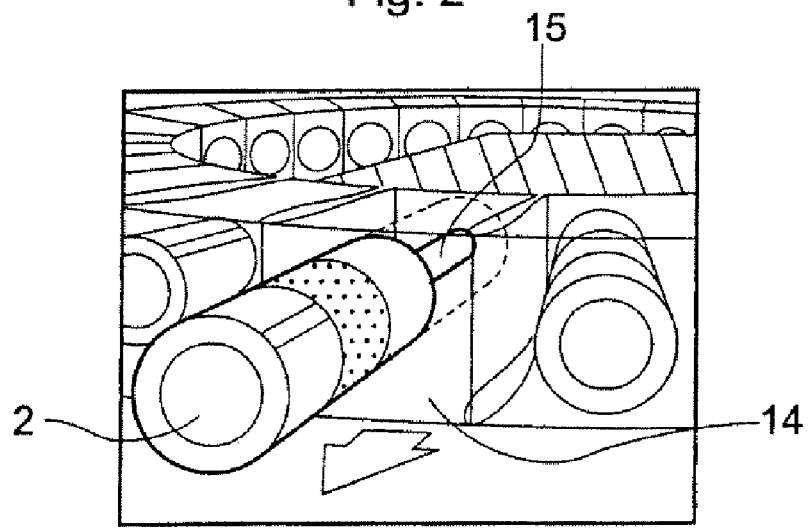
FIG. 3 is a schematic representation of the ejection of a spool from the spool carrier.

With reference to FIGS. 2 and 3, a plurality of spools (2) and carriers (3) are joined in a disc to form a magazine. The plurality of dose units (1) arranged radially around the circumference of the magazine (14). The inhalation device is provided with a dispensing mechanism (not shown) and a push rod (15) which also acts radially. The push rod (15) when actuated operates in the radial plane of the magazine (14) ejecting a spool (2) radially from the spool carrier (3) into the inhalation passage (not shown). The spool (2) remains in the plane of the magazine (14) and the flange (7) remains in co-operation with the spool carrier (3) so that it can move out of the inhalation passage upon rotation of the magazine (14).

With reference to FIGS. 4 and 5, a "double decker" arrangement is achieved by joining a first magazine (14) with a second magazine (16). The inhaler mechanism is provided with a first push rod (5) and a second push rod (17). The push rods may be actuated jointly, separately or sequentially optionally allowing medicament to be dispensed at the same time in the spool from the first magazine (14) as in the spool from the second magazine (16).

Figure 6:
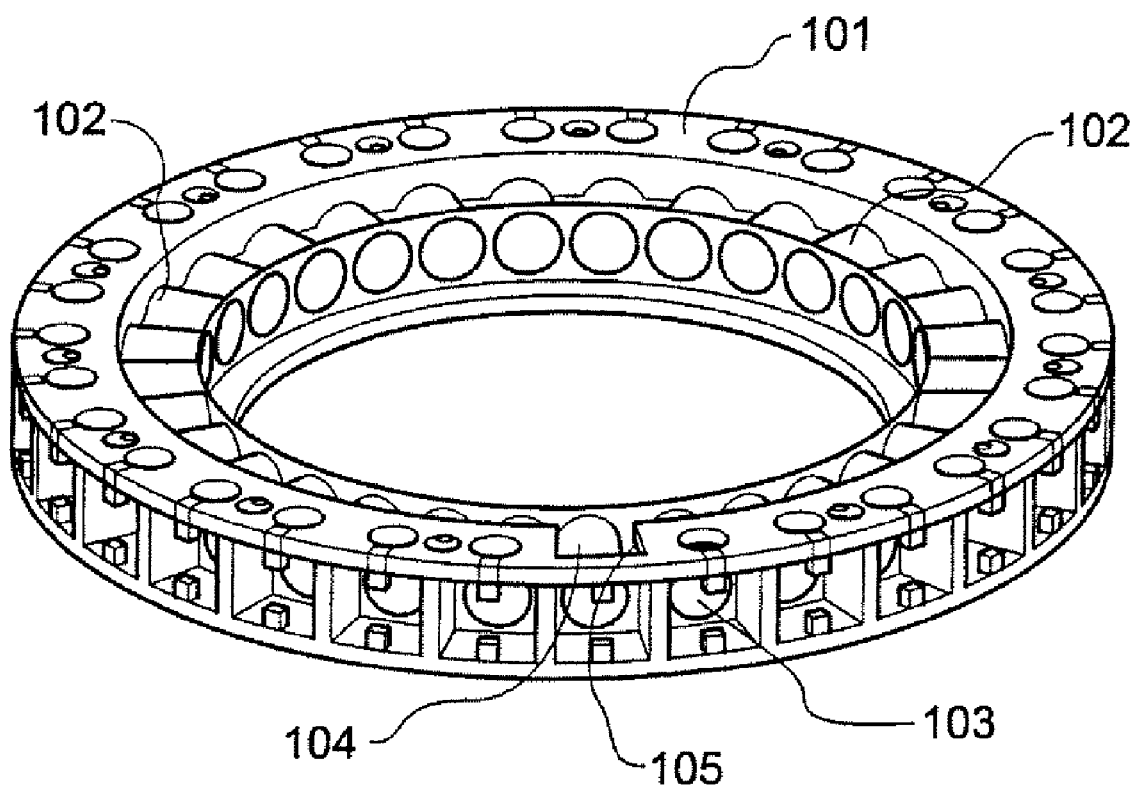
FIG. 6 is a perspective view of a disc magazine provided with an empty spool holder.

With reference to FIG. 6, a spool carrier magazine (101) comprises a disc provided with a plurality of radially mounted spool carriers (102). Each of the spool carriers (102) (save for one) is provided with a spool (103). One of the spool carriers (104) is empty and is provided with a cut away portion (105).

Figure 7:
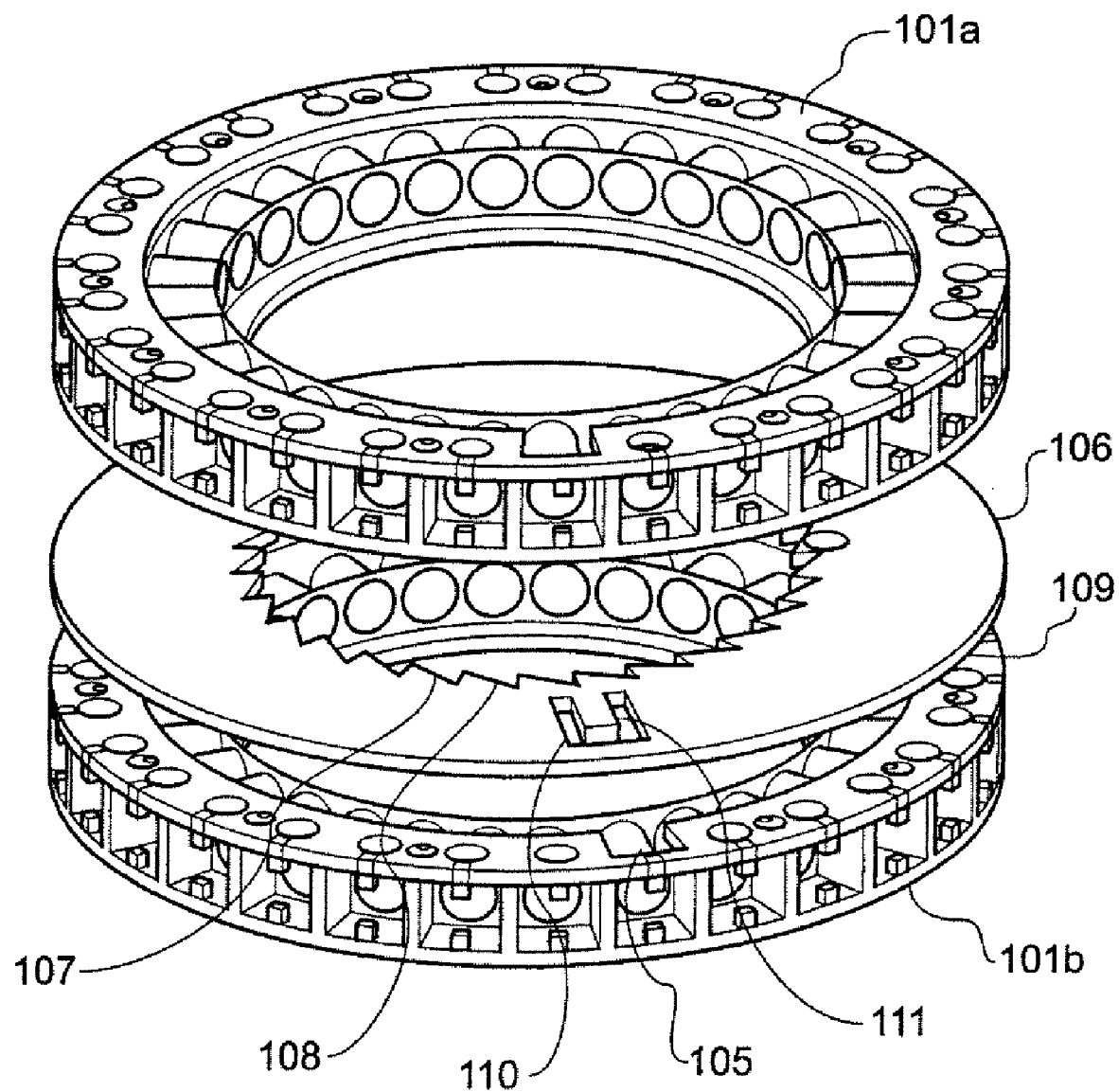
FIG. 7 is a perspective view of a pair of disc magazines provided with a drive plate.

With reference to FIG. 7, a pair of spool carrier magazines (101a and 101b) are provided. A drive disc (106) comprises a substantially planar annular disc. The inner surface (107) of the drive disc (106) is provided with a plurality of teeth (108) which are adapted to engage with a drive means (not shown).

Adjacent to the periphery (109) of the drive disc (106), the disc is provided with an aperture (110) through which protrudes an out of plane resilient male member (111). The male member (111) is biased towards one of the magazines. By way of example only, the embodiment described is one in which the male member (111) is biased towards the uppermost magazine (101b), although it should be understood that the present application should be read to also encompass an embodiment in which the male member may be biased towards the other magazine (101a).

The drive disc (106) is positioned adjacent to the first magazine (101b) such that the male member (111) overlies the cut away portion (105) and the empty spool carrier (104). When the second magazine (101a) is positioned in place it is arranged such that a filled spool carrier (102) overlies the male member (111). The circumferential surface rests against the male member (111) and urges it into an engaging position with the empty spool carrier (104).

Thus, in use, when the annular drive disc (106) is rotated, the male member (111) engages with the empty spool carrier (104) to rotate the first magazine (101b) whilst the second magazine (101a) is disengaged and therefore remains unmoved.

Figure 8:
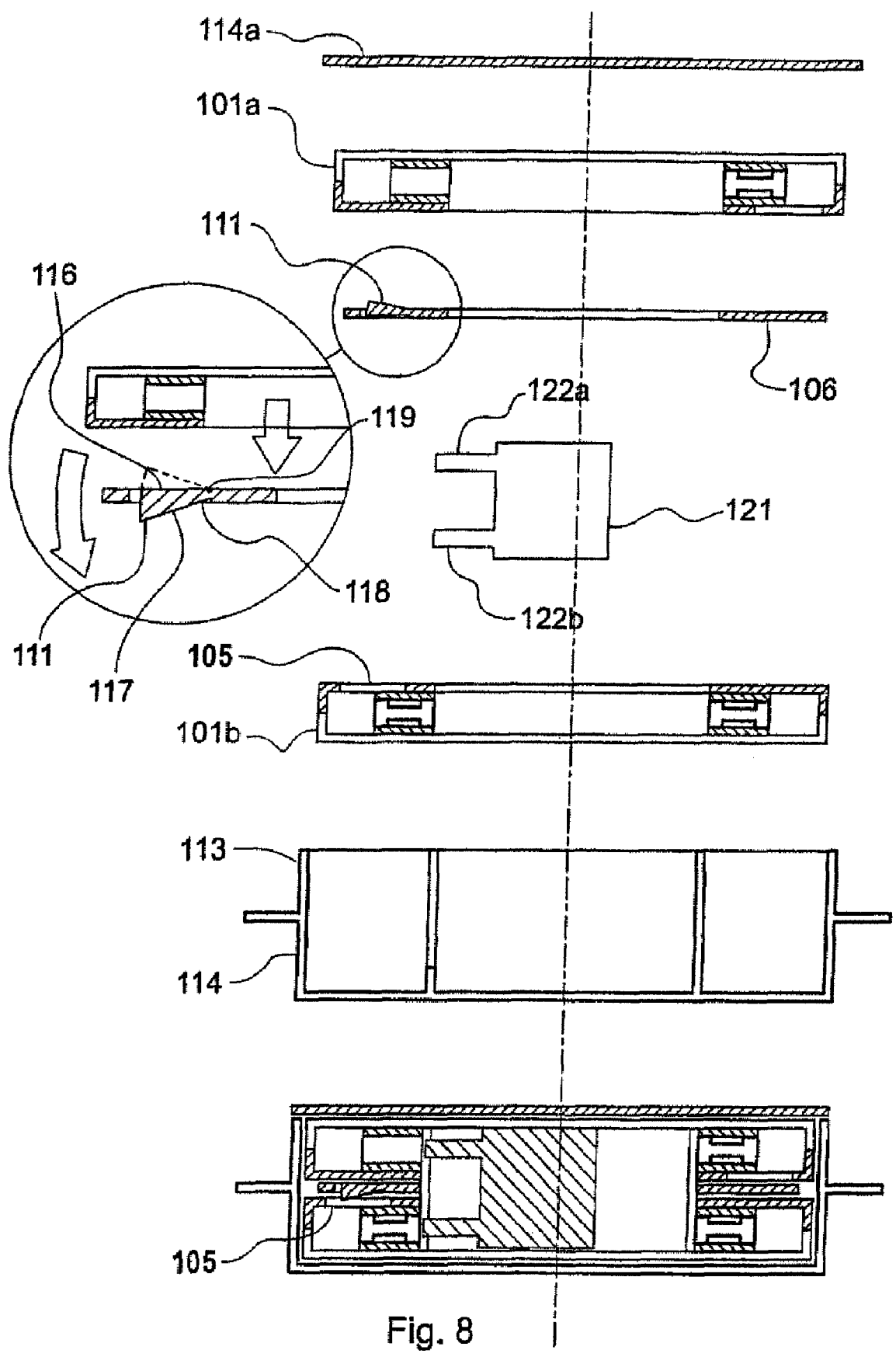
FIG. 8 is a schematic representation of a pair of magazines provided with a drive plate.
Figure 9:
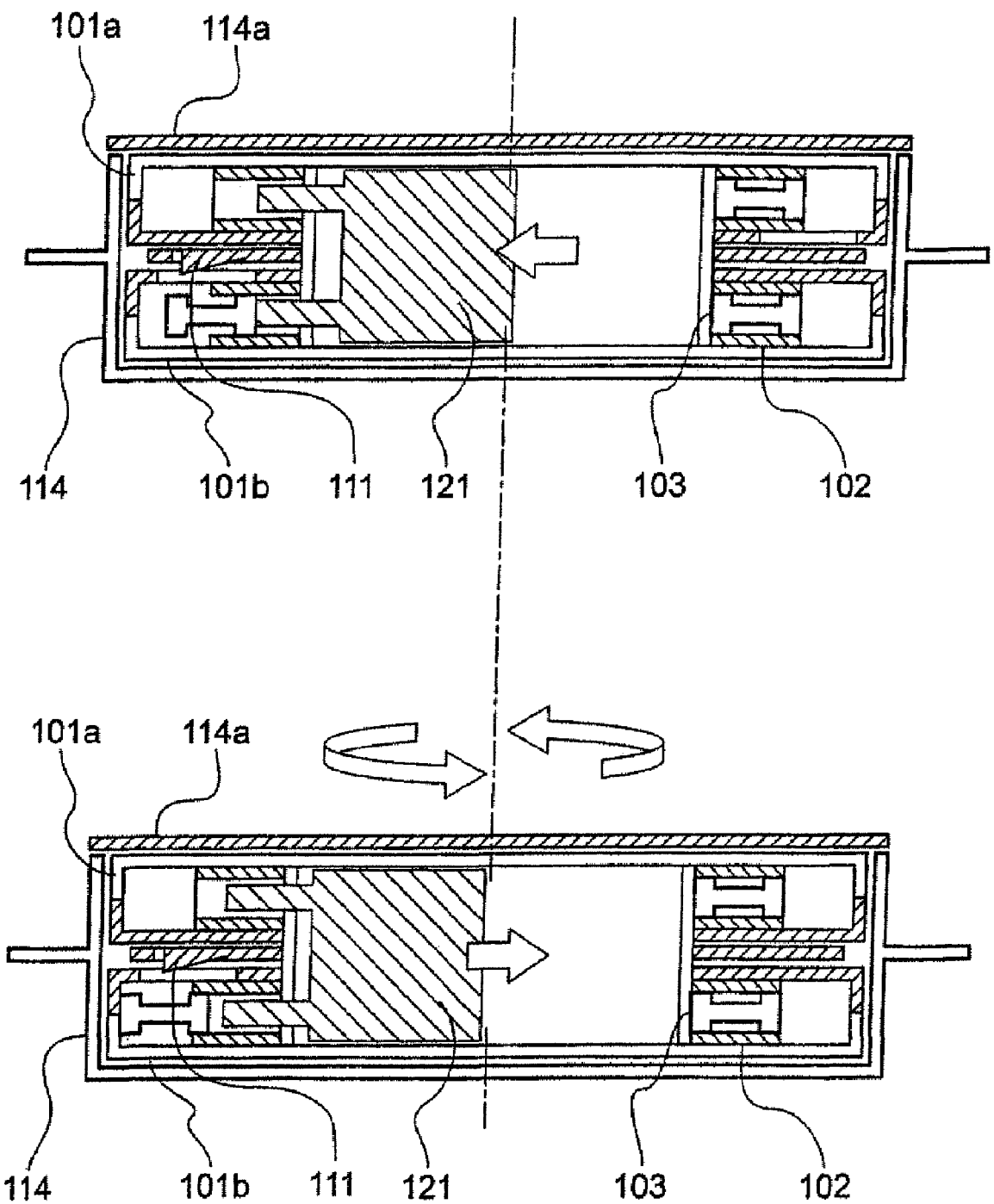
FIG. 9 is a schematic representation of the carousel in operation with dual plunger rods.
Figure 10:
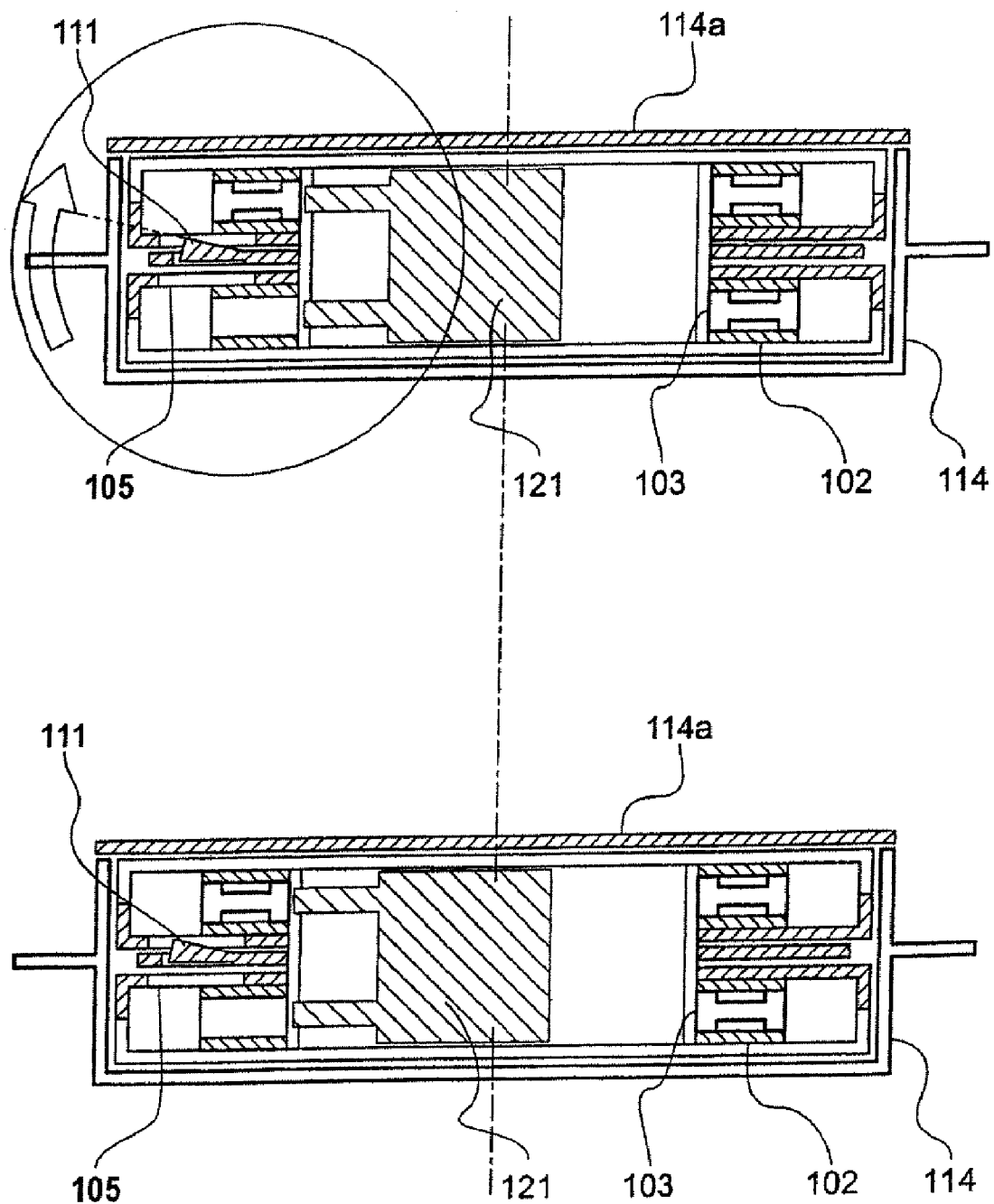
FIG. 10 is a schematic representation of the device when the first (lower) carousel has completed a 360° rotation.
Figure 11:
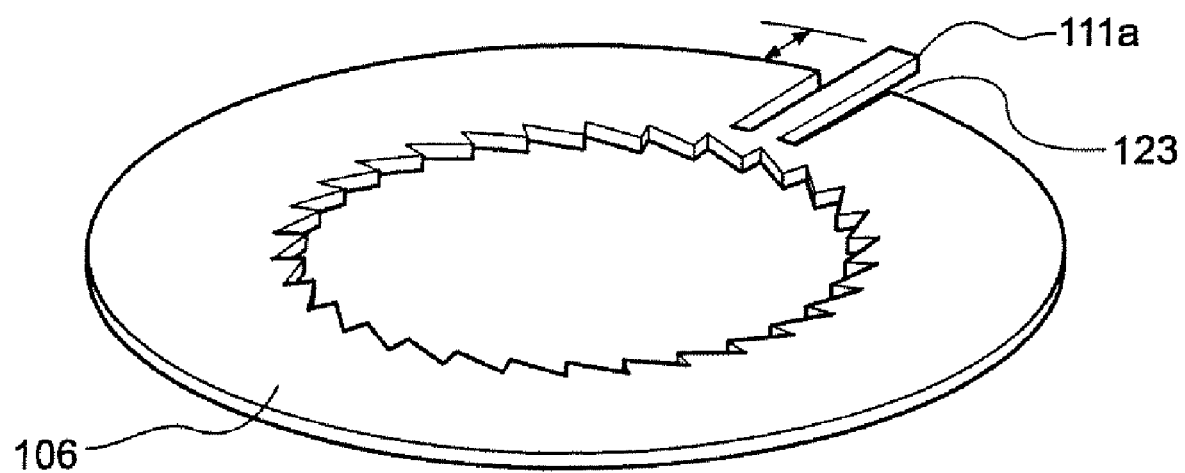
FIG. 11 is a perspective view of an alternative embodiment of a drive disc.
Figure 12:
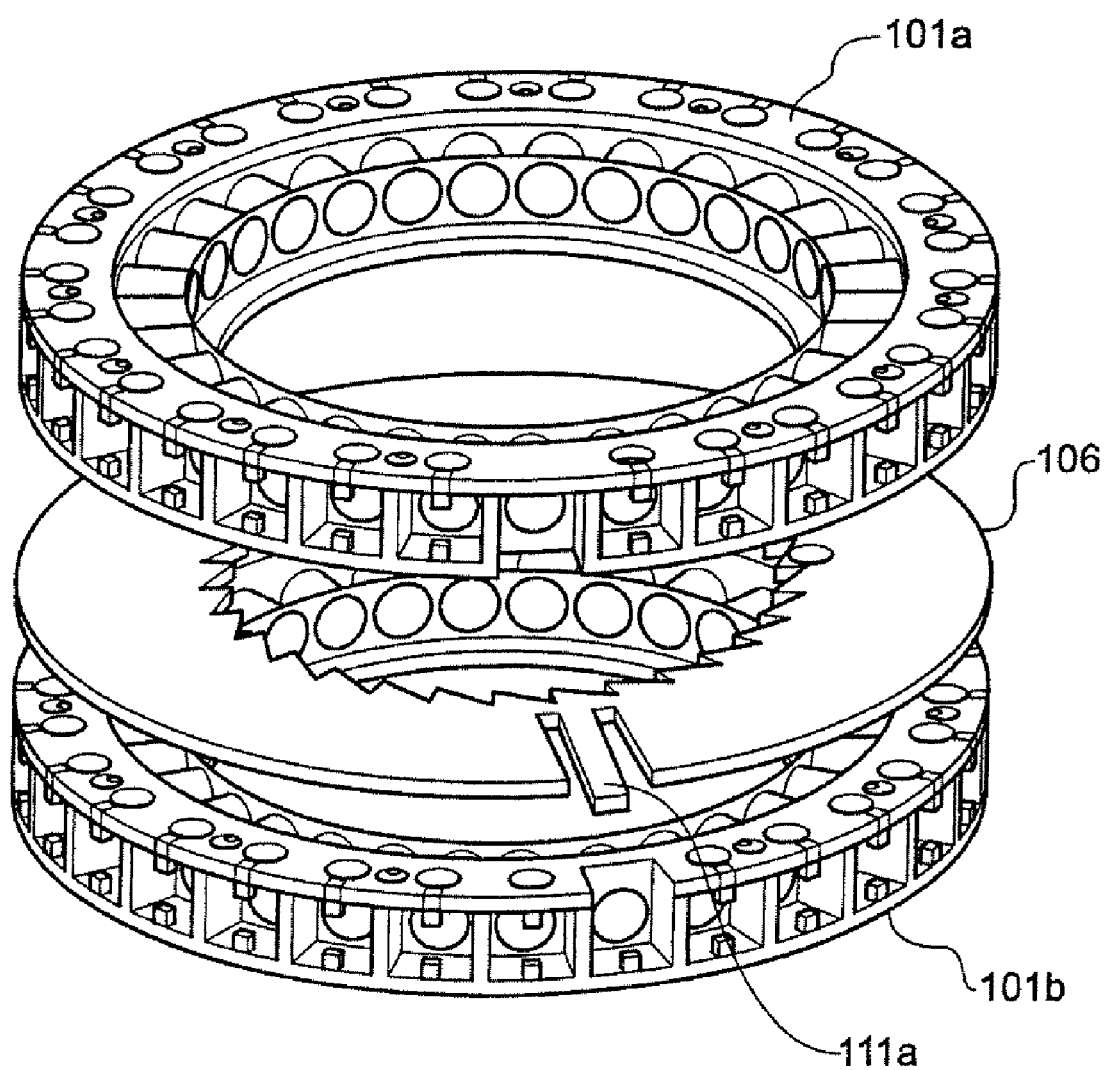
FIG. 12 is a perspective view of a pair of disc magazines with a drive disc.
Figure 13:
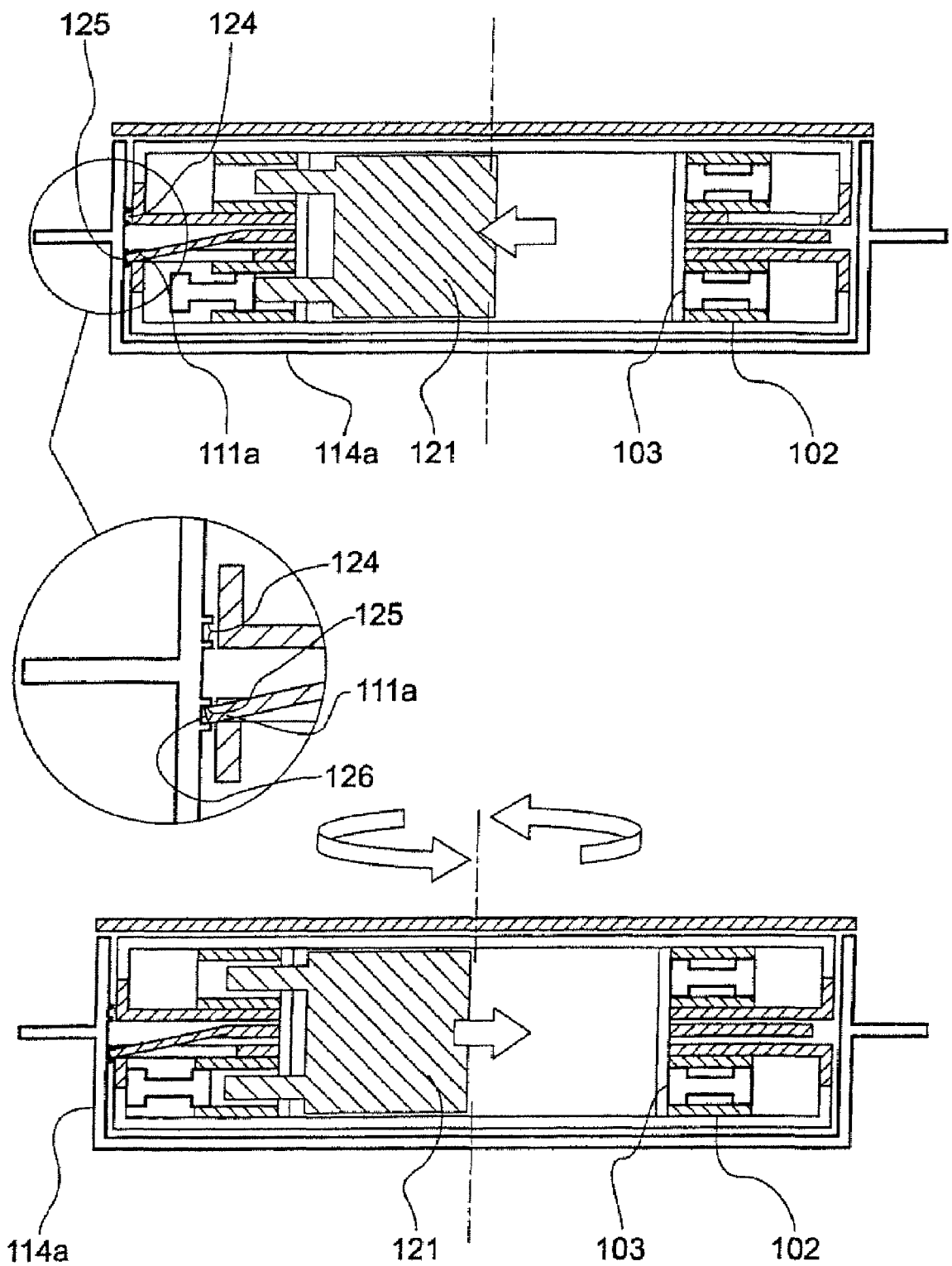
FIG. 13 is a schematic representation of a device in operation with a dual plunger rod.
Figure 14:
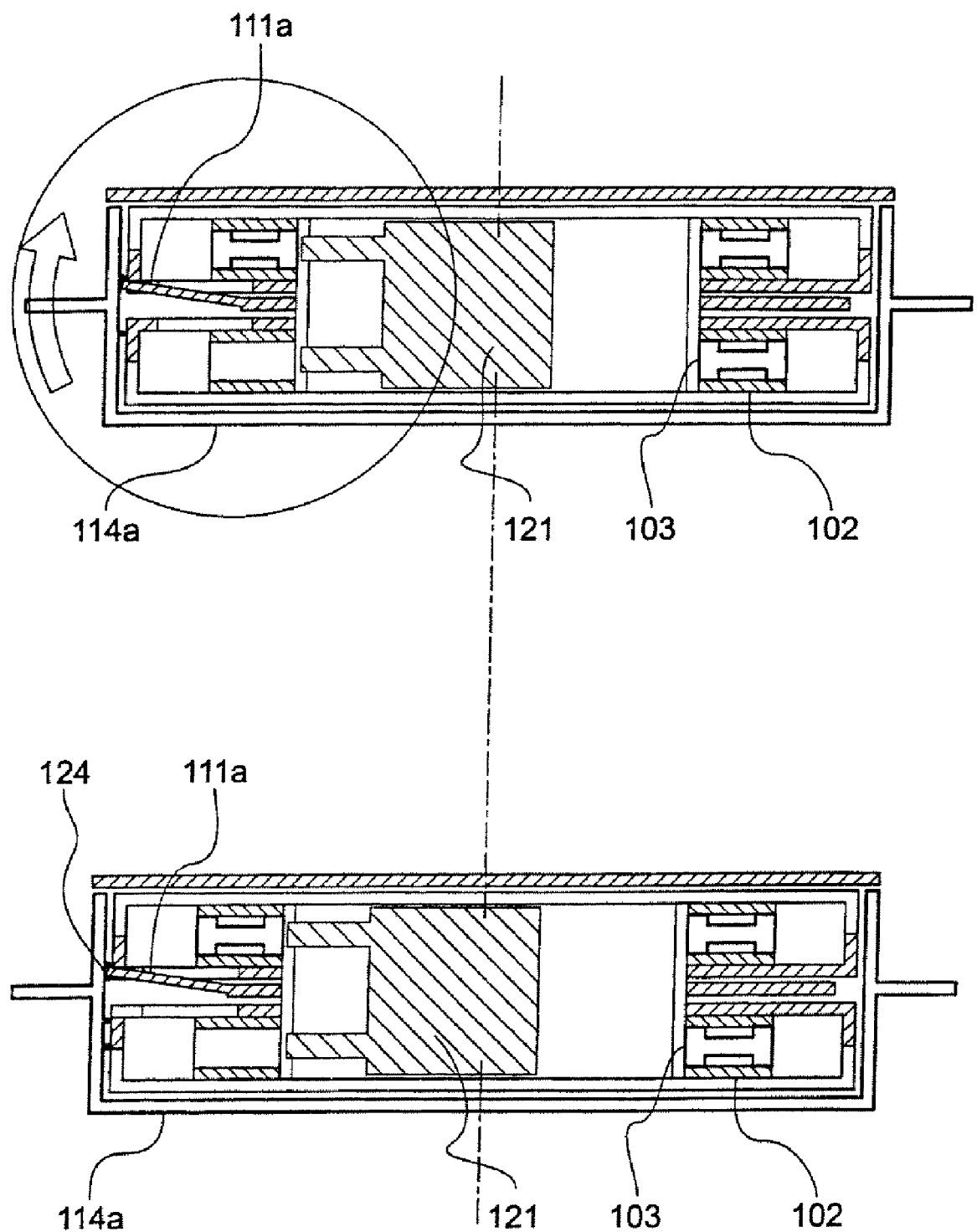
FIG. 14 is a schematic representation of a device when the first (lower) carousel has completed a 360° rotation.

With reference to FIGS. 8-10, the assembly of the system is illustrated. Thus, the assembly (113) comprises a chassis (114) and the drive disc (106) is placed above the magazine (101b). The male member (111) is biased away from the magazine (101b) and therefore protrudes above the plane of the drive disc (106). The second upper magazine (101a) is then positioned above the drive disc (106).

The male member (111) comprises a substantially triangular shaped tab with a first surface (117), a second surface (116), a hinged end (118) and a distal end. Optionally, the hinged end (118) may be provided with a groove (119) to facilitate the flexible movement of the male member (111). In its free position the male member (111) rests such that the first surface (117) lies in the plane of the drive disc (106) and the second surface (116) lies out of the plane and protrudes from the drive disc (106).

When the second, upper magazine (101a) is in place, the lower, outer surface of the spool carrier magazine is urged against the second surface (116) of the male member (111). This urges the second surface (116) to lie in the plane of the drive disc (106) and therefore the first surface (117) lies out of the plane, enabling it to engage with the empty spool carrier (104).

A push rod (121) is also provided which comprises a pair of spool prodders (122a and 122b). The push rod (121) is connected to an actuator means (not shown). A chassis lid (114a) is provided to close the system.

With reference to FIGS. 11 to 14, a further embodiment is illustrated in which the male member (111a) protrudes beyond the peripheral edge (123) of the drive disc (106). The chassis (114a) is provided with two sets of guide rails (124 and 125). The device is assembled so that the male member (111a) is tensioned and the peripheral end (126) of the male member (111a) held in the guide rail (125). When the lower magazine has rotated through approximately 360°, the male member (111a) reaches a break in the guide rails (124 and 125), thus allowing the male member (111a) to be urged towards the second magazine and into the second guide rail (124).

The invention claimed is:

1. A delivery device comprising a first rotatable magazine and a second rotatable magazine, each magazine being provided with a plurality of metering members adapted to dispense a measured amount of material, a material delivery passage and a material delivery orifice, and at least one push rod adapted to move a metering member from a material retaining position to a material dispensing position, wherein the device is provided with means for engaging the first magazine whilst disengaging the second magazine and which engaging means is moveable from an engaging to a disengaging position and vice-versa.

2. A delivery device according to claim 1 characterised in that the material is a medicament.

3. A delivery device according to claim 2 characterised in that the medicament metering member comprises a spool and a spool carrier wherein the void between the spool carrier is filled with medicament.

4. A delivery device according to claim 3 characterised in that the device is provided with a pair of magazines and said pair of magazines contain the same medicament.

5. A delivery device according to claim 3 characterised in that the device is provided with a pair of magazines and said pair of magazines contain different medicaments.

6. A delivery device according to claim 2 characterised in that the medicament delivery device is an inhaler.

7. A delivery device according to claim 1 characterised in that the material is a dry powder.

8. A delivery device according to claim 1 characterised in that the magazine is substantially circular.

9. A delivery device according to claim 1 characterised in that the engaging means comprises male and female interlocking members.

10. A delivery device according to claim 9 characterised in that the magazine is provided with a female member and a drive means is provided with a male member.

11. A delivery device according to claim 10 characterised in that a drive plate is provided with a male member and is adapted to engage with the drive means.

12. A delivery device according to claim 11 characterised in that the male member comprises a resilient protrusion which is resiliently biased towards a second magazine, but is constructed so as to be urged to engage with a female member of a first disc magazine, such that when the urging means is removed the male member is biased towards and engages with the second magazine.

13. A delivery device according to claim 12 characterised in that the actuator means comprises at least two radially acting push rod mechanisms which may operate together, independently or sequentially.

14. A dry powder inhaler comprising a plurality of metering members adapted to dispense a measured amount of medicament and held in a first rotatable magazine and a second rotatable magazine, an inhalation passage and a mouthpiece, and at least one push rod adapted to move one of the plurality of metering members from a medicament retaining position to a medicament dispensing position, wherein the inhaler is provided with means for engaging the first magazine whilst disengaging the second magazine and which engaging means is moveable from an engaging to a disengaging position and vice-versa.

15. A dry powder inhaler according to claim 5 characterised in that the medicaments are fluticasone and salmeterol.

16. A dry powder inhaler according to claim 14 characterised in that the inhaler is provided with two push rods.

17. A method of administering a dry powder medicament using a delivery device according to claim 7.

18. A method according to claim 17 characterised in that a combination of medicaments are administered.

19. A method of treatment of a patient with a respiratory disorder comprising the administration of a therapeutically effective amount of a medicament using an inhaler according to claim 6.

* * * * *